United States Patent [19]

Crumm et al.

[11] 4,259,011
[45] Mar. 31, 1981

[54] OPTICAL GEM ANALYZER

[76] Inventors: John C. Crumm, 814 Alma Real Dr., Pacific Palisades, Calif. 90272; George D. Carlsen, 12536 Truro, Hawthorne, Calif. 90250

[21] Appl. No.: 91,473

[22] Filed: Nov. 5, 1979

[51] Int. Cl.³ .............................................. G01J 3/50
[52] U.S. Cl. ...................................... 356/30; 356/418
[58] Field of Search .................. 356/30, 31, 418, 419, 356/425, 443, 445; 250/226

[56] References Cited

U.S. PATENT DOCUMENTS

| 3,794,424 | 2/1974 | Eickhorst et al. ................... 356/418 |
| 4,076,424 | 2/1978 | Ida ..................................... 356/418 |

FOREIGN PATENT DOCUMENTS

| 2344144 | 3/1975 | Fed. Rep. of Germany ............. 356/30 |
| 2010474 | 6/1979 | United Kingdom ..................... 356/418 |

Primary Examiner—R. A. Rosenberger
Attorney, Agent, or Firm—Ralph B. Pastoriza

[57] ABSTRACT

Quantitative data concerning a gem such as a diamond is obtained by irradiating the gem with wide spectrum light. The internal reflections and refractions of this light are picked up and passed through different filters, the output intensity of light from various filters being compared to a reference output from a reference filter. The output data from the examined light provides information as to the quality of the gem.

4 Claims, 3 Drawing Figures

OPTICAL GEM ANALYZER

This invention relates generally to optical equipment and more particularly to a gem analyzer for providing quantitative readings indicative of the quality of a gem.

BACKGROUND OF THE INVENTION

The quality of valuable gems such as diamonds, rubies, sapphires, emeralds and the like is determined largely in a subjective manner. More particularly, persons allegedly skilled in the art will examine a gem with a magnifying eye piece looking for flaws and the like and will then express an opinion as to the quality of the gem and its value. About the only parameter that is not subjective is the weight of the gem itself.

While the above referred to "experts" may provide fairly consistent estimates as to a gem's quality, there is often a wide variation wherein the same gem is examined by two totally different "experts". Again, about the only parameter that the two experts will find in common is the weight of the gem.

As a consequence of the foregoing manner of evaluating gems, and the fact that any estimate as to worth based on the quality of the gem is largely dependent upon the particular person analyzing the gem, great disparities can exist in proper evaluation of a gem, particularly where the evaluators themselves are widely spaced geographically or come from other countries where different techniques might be used.

BRIEF DESCRIPTION OF THE PRESENT INVENTION

Bearing the foregoing considerations in mind, the present invention contemplates the provision of special optical equipment so designed as to provide some output parameters characteristic of certain gems which can be used for quality determinations in an objective manner, all to the end that a more consistent gem evaluation can be realized.

In accord with the broadest aspects of this invention, the gem analyzing equipment includes a wide spectrum light source together with means for holding the gems to be analyzed in a fixed position relative to the light source. Appropriate filter means including a reference filter and at least one other filter are respectively positionable to intercept light passing from the gem resulting from internal reflections and refractions of light passing into the gem from the referred to light source. Means are then provided responsive to the intensity of light from the reference filter and from at least said one other filter to provide a reference reading for comparison with a reading from the said at least one other filter, respectively, and thereby yield information as to the quality of the gem.

BRIEF DESCRIPTION OF THE DRAWINGS

A better understanding of this invention as well as many further features and advantages thereof will be had by now referring to the accompanying drawings in which.

Figure 1:
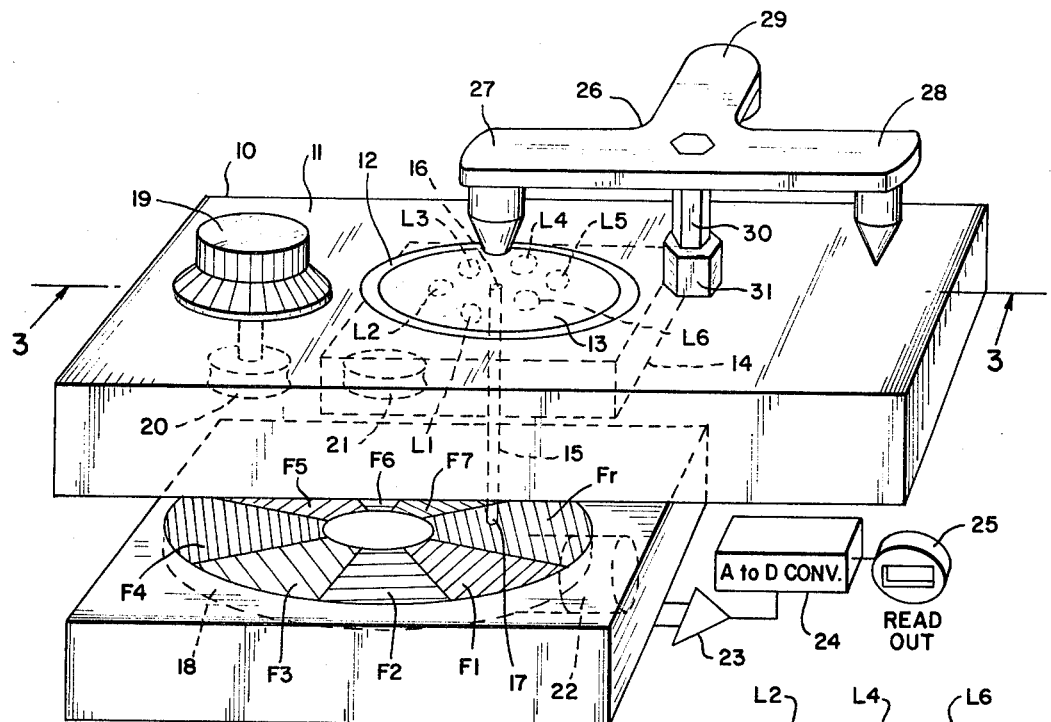
FIG. 1 is a perspective view diagramatic in nature and utilizing phantom lines to indicate hidden components of the system showing the gem analyzer of this invention.

From research studies conducted long prior to the development of the present invention, it was found that certain gems exhibit certain absorption spectra for light and such absorption spectra within certain wave length bands are constant from sample to sample. On the other hand, for a different wave band region of light, differences between similar type gems become evident.

In the case of diamonds, the absorption spectra is fairly consistent from sample to sample in the region from 6,000 to 7,000 Angstroms. On the other hand, differences in the absorption spectra show up from comparison of the same samples in wave length regions from 3,000 to 5,000 Angstroms.

The foregoing characteristics will provide a means to generate quantitative information concerning a gem so as to realize the desired goal of providing consistent evaluations for any given gem sample of a given weight.

The manner in which advantage is taken of the foregoing in accord with the present invention will now be described by referring first to FIG. 1 wherein the optical gem analyzer according to this invention includes a housing 10. On the top surface 11 of the housing 10 there is provided a cut-out area 12 within which there is positioned a translucent member 13 defining a light emitting surface.

As indicated clearly in both FIGS. 1 and 3, there is provided a light box 14 below the translucent member 13 having light source means for passing light to the translucent member. In the preferred embodiment described, the light source is such as to cover a wide spectral band so that in the analysis of a gem, the light source will include spectral bands between 6,000–7,000 Angstroms and 3,000–5,000 Angstroms.

We have discovered that a most effective light source for accomplishing the foregoing can be provided by simple tungsten filament flashlight like bulbs or lamps operating at fairly high temperatures.

Figure 3:
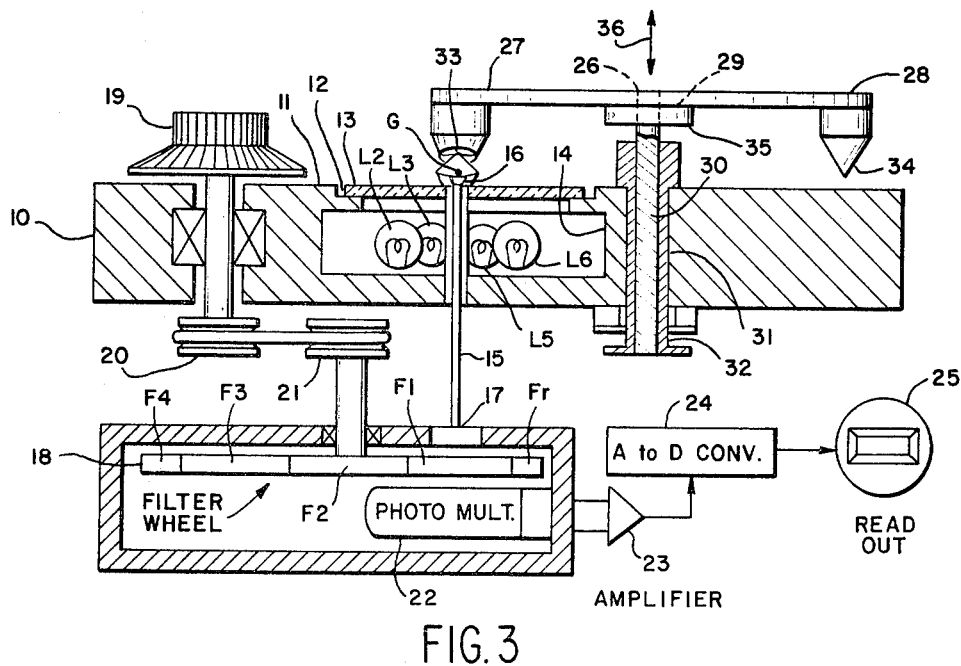

In both FIGS. 1 and 3, the light source is shown as comprising six such incandescent type of bulbs labeled "L1, L2, L3, L4, L5 and L6". These tungsten filament lamps as shown are arranged in a symmetrical circular pattern beneath the translucent member 13.

A fiber optic bundle 15 extends downwardly from a center point 16 on the light emitting surface 13 to a remote position such as indicated at 17 outside of the light box portion 14. The various light source tungsten filament lamps L1 through L6 surround symmetrically the fiber optic bundle 15 but the bundle itself is completely shielded from light from these lamps. The only light received by the fiber optic bundle 15 is that reradiated from the gem to be analyzed which gem itself receives light passing through the translucent member 13.

By way of example, there is shown a gem G positioned precisely on the point 16 and held in this consistent position. Light from the various lamps passing through the translucent member 13 will be received by all of the facets of the gem G and be internally reflected and refracted, a portion of this light passing back down through the fiber obtic bundle 15.

To assure that there is relatively even radiation about the entire circumference of the gem, the lamps are arranged in the circular pattern as described symmetrical with a vertical axis passing through the center point 16. Moreover, balanced light effects are assured by energizing two strings of the lights connected in parallel. Each string has three light filaments in series constituting alternate ones of the lights in the referred to circular array of the lights shown in phantom in FIG. 1. This arrangement provides for a balanced lighting even though the voltage drop across one string may vary from that across the other.

Figure 2:
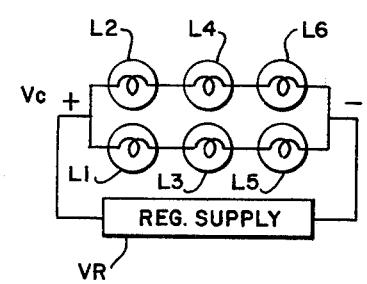
FIG. 2 is an electrical circuit diagram useful in explaining the preferred manner of providing a light source in accord with the present invention; and, FIG. 3 is a cross section with certain portions shown in full lines looking in the direction of the arrow 3—3 of FIG. 1.

FIG. 2 is a simple electrical diagram of the referred to two strings of lights, bulbs L1, L3 and L5 being in one string and the remaining lamps L2, L4 and L6 being in the other string. The voltage across the strings is indicated by $V_c$ and is derived from a carefully regulated supply indicated VR in FIG. 2. It will be seen because of the alternate positioning of the lamps relative to the string shown in FIG. 2 that should the voltage drop across one string different from that of the other, there still will result balanced lighting.

Referring once again to FIGS. 1 and 3 together, there is provided a light filter means in the form of a filter wheel 18 having, in the preferred embodiment disclosed, seven distinct filters in addition to a reference filter. Thus, the wheel, as shown, is oriented to intercept light from the fiber optic bundle 15 exiting from the remote point 17. The referred to reference filter is indicated $F_r$ while the other filters are indicated at F1 and F7.

The arrangement is such that selected ones of the filters can be positioned to intercept light from the end 17 of the fiber optic bundle 15. Such selection in the specific example shown for illustrative purposes can be effected manually by rotating an appropriate knob 19 mounted in the housing 10 which will rotate the filter wheel 18 through appropriate pulleys 20 and 21.

On the other side of any one filter positioned beneath the light exit point 17 from the fiber optic bundle 15 is a photo multiplier tube 22. This photo multiplier tube will provide an output signal constituting a function of the intensity of light emanating from the lower side of any selected one filter. This signal is amplified by an appropriate amplifier 23 and thence passed through an analog to digital converter 24. The output of the analog-to-digital converter is passed into an appropriate read-out 25 which may comprise light emitting diodes or liquid crystals. The read-out itself is in the form of numerals or numbers which provide a value for a given light intensity.

From the foregoing, it will be evident that a first reading can be taken with the reference filter $F_r$ in position to intercept light passing down the fiber optic bundle 15. A subsequent reading is then taken when at least one of the other filters is positioned to intercept light passing down the fiber optic bundle and the read-out provided by this other filter is compared with that provided when the reference filter is in position. The difference between these read-outs will constitute an indication as to the quality of the gem.

In order that consistent readings be obtained for any one gem, there must be provided an appropriate means for holding the gem in a consistent face down position on the light emitting surface over the referred to center point 16. Such means in accord with the present invention is illustrated in both FIGS. 1 and 3 in the form of a turret structure 26 having three stages 27, 28 and 29. Any one of these three stages can be positioned precisely over the center point 16 of the translucent member 13.

Moreover, the entire turret can be raised vertically so that the distance from the underside of any one stage from the center point 16 can be varied to accommodate gems of a different size.

With respect to the foregoing vertical adjustment, it will be noted that the turret 26 is mounted on a vertical shaft 30 preferably of a non-circular cross section such as a hexagonal cross section as shown. The hexagonal shaft 30 is arranged to move up and down within a correspondingly shaped hexagonal socket 31. By providing the non-circular cross section or hexagonal shape for the shaft and the receiving socket or cylinder, rotation of the shaft 30 within the socket or cylinder is prevented. On the other hand, the entire shaft and socket structure can be rotated as a unit and properly indexed to the various positions to properly center a selected stage over the center point 16.

The foregoing indexing can be accomplished by a simple ball detent 32 shown on the underside of the housing 10 in FIG. 3, the outer cylinder or socket 31 carrying the indexing ball 32 which ball is received in appropriate detents properly spaced and secured on the bottom of the housing 10.

The first stage 27 shown positioned over the center point 16 in both FIGS. 1 and 3 has a concave bottom surface indicated at 33 in FIG. 3.

If the gem is of a different type or is in a mounting, it might be more readily held by the second stage 28 which includes a downwardly directed sharp point 34.

The third stage 29 comprises a convex calibrating mirror 35 shown best in FIG. 3. This mirror will direct light from the translucent light source down through the center opening to pass into the fiber optic bundle for calibrating purposes.

When the calibrating mirror 35 is used, it will be positioned at a consistent vertical distance above the central point 16 on the light emitting surface or translucent member 13. Normally, this position might be the lowest position assumed by the turret. Raising of the turret to a higher position to accommodate various types of gems is indicated by the double headed arrow 36 in FIG. 3.

OPERATION

Referring still to both FIGS. 1 and 3, in operation the third stage 29 containing the convex calibration mirror 35 is initially positioned over the center point 16 on the light emitting surface with the turret structure in its lowest vertical position. In this calibration position, the filter wheel 18 is now manually rotated from segment to filter segment starting with the reference filter $F_r$. The output read-out 25 is checked in each filter position for a full scale indication. If such full scale indication does not result, appropriate adjustments are made to calibrate the same to provide such full scale indication.

After calibration is complete, the next step is to place a stone or gem to be analyzed face-down directly on the central point 16 of the light emitting surface 13. The appropriate arm 27 or 28 of the hold down fixture or turret is rotated in a position over the stone or gem and carefully lowered to hold the same in position.

Preferably, the entire top of the housing and turret structure is cloaked with light opaque material to keep out ambient light. The light source in the form of the light bulbs L1 through L6 is then energized so as to pass light from the light emitting surface into all of the facets of the gem, this light being internally refracted and reflected such that a large portion thereof is transferred by the fiber optic bundle 15 from the center point 16 over which the gem is positioned to the remote point 17.

The filter wheel is again initially positioned with the reference filter in position to intercept the light from the gem. A reading is taken with the reference filter in position from the read-out 25. The filter wheel is then moved to the next successive position for successively causing the various filters F1 through F7 to intercept light from the end 17 of the fiber optic bundle 15. Appropriate readings are taken for each of the filter positions from the read-out.

Comparison of the readings with that obtained from the reference reading produces data indicative of the absorption on the selected spectrum areas and thus can be used to indicate the quality of the gem.

A very desirable feature of this invention is the provision of repeatable results. So long as the same gem is consistently positioned by the hold-down or turret structure, rerunning the test even wherein such tests are made at widely spaced time intervals, provides very consistent readings so that with optical equipment as described at widely spaced locations, a gem can be consistently analyzed and a uniform value placed on it.

From all of the foregoing, it will thus be evident that the present invention has made an important contribution to the evaluation of precious stones.

While the particular gem analyzer was described in conjunction with the analysis of diamonds, it can clearly be used for the analysis of other gems wherein different spectral regions are involved. Appropriate different types of filters would be used for the different types of gems to optimize the obtainable data.

The gem analyzer is accordingly not to be thought of as limited to the specific example set forth for illustrative purposes.

We claim:

1. An optical gem analyzer including, in combination:
   (a) a housing having on its top surface a cut-out area;
   (b) a translucent member in said cut-out area defining a light emitting surface;
   (c) a light box in said housing below said translucent member having light source means passing light to said translucent member;
   (d) a fiber optic bundle extending downwardly from a center point on said light emitting surface to a remote position outside said light box;
   (e) a light filter means having a reference filter and at least one other light filter in said housing;
   (f) means for selectively positioning any one of said filters in a position to intercept light passing from the end of said fiber optic bundle at said remote location;
   (g) a photo multiplier detector positioned to receive light passing through said selected filter;
   (h) read-out means connected to said photo multiplier to provide a read-out indicative of the intensity of light after passing through said filter; and
   (i) a three-stage turret structure mounted on said housing such that each stage can be positioned directly over said center point on said light emitting surface and moved axially in an up and down direction, a first stage having a concave surface for holding a gem in a consistent face-down position in engagement with said light emitting surface over said center point, a second stage having a pointed convex surface for holding a different type of gem in a mounting, and a third stage comprising a convex calibrating mirror for directing light from said light emitting surface down through said center opening to pass into said fiber optic bundle for calibrating purposes, whereby said gem when held in said first stage will receive light from said light emitting surface on all of its facets surrounding said center point, said light being internally reflected and refracted and at least a portion thereof passing through said center point from inside said gem to be transmitted by said fiber optic bundle to said remote position and pass through a selected filter so that a comparison of said read-out when said light passes through said reference filter can be made with the read-out when said light passes through said at least one other filter to thereby provide an indication of the gem quality.

2. An optical gem analyzer according to claim 1, in which said light source means in said light box comprises six tungsten filament lamps arranged in a symmetrical circular pattern about the vertical axis of said center point; and a regulated voltage supply for energizing two strings of the lights connected in parallel, each string having three light filaments in series constituting alternate ones of the lights in said circular array to thereby provide a balanced lighting even though the voltage drop across one string may vary from that across the other, said lamps emitting radiation including the spectrum from 7,000 to 3,000 Angstroms.

3. An optical gem analyzer according to claim 1, in which said light filter means includes in addition to said reference filter seven additional filters for passing different spectral bands of light from the end of said fiber optic bundle, said spectral bands falling within the range of 7,000 to 3,000 Angstrom units, said filters being mounted on a circular wheel, and, manually rotatable means on the top surface of said housing coupled to said wheel to enable manual positioning of a selected filter for interception of light passing from the end of said fiber optic bundle.

4. An optical gem analyzer according to claim 1, in which said read-out means includes an amplifier connected to the output of said photo multiplier tube, an analog-to-digital converter connected to receive the output from said amplifier, and a digital read-out means connected to the output of said analog-to-digital converter for providing a numeric indication of the intensity of light passing through the selected filter.

* * * * *